United States Patent [19]

Steinhards

[11] 3,999,975
[45] Dec. 28, 1976

[54] HERBICIDAL COMPOSITIONS

[75] Inventor: Arnolds Steinhards, Kalamazoo, Mich.

[73] Assignee: The Upjohn Company, Kalamazoo, Mich.

[22] Filed: Jan. 30, 1970

[21] Appl. No.: 7,226

[52] U.S. Cl. .................... 71/95; 71/66; 71/64; 71/67
[51] Int. Cl.$^2$ ........................... A01N 9/22
[58] Field of Search ......................... 71/95

[56] References Cited
UNITED STATES PATENTS

| | | | |
|---|---|---|---|
| 3,541,111 | 11/1970 | Gerike | 71/95 X |
| 3,922,163 | 11/1975 | Church et al. | 71/95 |

OTHER PUBLICATIONS

*Plant Regulators*, CBCC Positive Data Series No. 2, June, 1955, pp. a, b, c & 41 (Au 124).
Kuster, *Zeitfur, Physiol.* Chemie 121. p. 135 (1922).
Thompson et al., *Botanical Gazette*, 107, pp. 475–507 (p. 497 of interest) 1946.

*Primary Examiner*—Glennon H. Hollrah
*Attorney, Agent, or Firm*—John J. Killinger; Carl A. Randles, Jr.; Roman Saliwanchik

[57] ABSTRACT

A known compound, 2-ethyl-4-methyl diester of 3,5-dimethyl-2,4-pyrroledicarboxylic acid, has been found to be an excellent herbicide. A new method of controlling weeds and growth of plants with the compound is described along with herbicidal compositions.

5 Claims, No Drawings

HERBICIDAL COMPOSITIONS

SUMMARY OF THE INVENTION

This invention pertains to a new method for controlling weeds, and to new herbicidal compositions. The invention is more particularly directed to a new method for controlling weeds and growth of plants with the compound 2-ethyl-4-methyl diester of 3,5-dimethyl-2,4-pyrroledicarboxylic acid; and to new herbicidal compositions containing the same.

The 2-ethyl-4-methyl diester of 3,5-dimethyl-2,4-pyrroledicarboxylic acid has the structural formula:

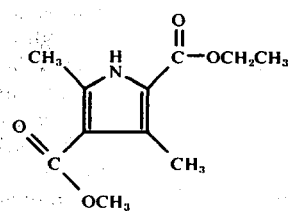

The compound is prepared according to the procedure described by W. Küster, Zeit. für physiol. Chemie 121, p. 135 (1922).

DETAILED DESCRIPTION OF THE INVENTION

The compound, 2-ethyl-4-methyl ester of 3,5-dimethyl-2,4-pyrroledicarboxylic acid, has been found to be especially active against broadleaf weeds when applied postemergence. It is also active when applied preemergence. The compound can be used to prevent damage to aesthetic and field crops due to weed competition, and it can be used to prevent unsightly and deleterious growths of weeds on home lawns, golf courses, cemeteries, railroad rights-of-way, in parks, and bodies of water.

For purpose according to the method of this invention, 2-ethyl-4-methyl diester of 3,5-dimethyl-2,4-pyrroledicarboxylic acid is formulated in herbicidal compositions. Such compositions in accordance with the invention include solutions, emulsions, suspensions, dispersible powders, emulsifiable concentrates, granular formulations, and dusts. All of these compositions comprise the compound in dispersed or readily dispersible form with a dispersible carrier, and with or without adjuvants. In general, selective inhibition of undesired weed species in the presence of field crops or in turf is obtained by employing a phytonomic carrier, that is to say, a carrier which can be applied to plants without phytotoxicity or other adverse effects. On the other hand, when general herbicidal activity is desired a phytotoxic carrier, for example, high-boiling mineral oil fractions or polychlorinated hydrocarbons such as tetrachloroethane can be used.

The efficacy of 2-ethyl-4-methyl diester of 3,5-dimethyl-2,4-pyrroledicarboxylic acid as a herbicide is of high order, and the compound can be applied at relatively low rates per acre for controlling growth of weeds and other plants. Illustratively, the compound gave complete or substantially complete suppression of buckhorn plantain (*Plantago lanceolata L.*), common purslane (*Portulaca oleracea L.*), yellow foxtail (*Setaria glauca L.*), bindweed (*Convolvulus arvensis*), lambsquarters (*Chenopodium album*), and red sorrel (sheep sorrel) (*Rumex acetosella L.*), when applied at rates of about 6 lbs. per acre. Rates of application of about 0.5 to about 15 lbs. per acre are efficacious under usual conditions, depending upon the particular circumstances such as growth response desired, type of soil, amount of rainfall or irrigation, and the most prevalent kinds of weeds. At the high rates of application, e.g., at 20 to 50 lbs. per acre the compound acts as a soil sterilant.

Illustratively, excellent control of weeds in rice fields has been obtained, without significant damage to the rice plants, using concentrations of 2-ethyl-4-methyl diester of 3,5-dimethyl-2,4-pyrroledicarboxylic acid, ranging from about 1000 ppm (parts per million) to about 5000 ppm applied at the rates of about 1 lb. to about 3.0 lbs. per acre. In general, a desired rate of application can be achieved by distributing, over the area to be treated, an aqueous composition in accordance with the invention, containing from about 700 ppm to about 30,000 ppm of active ingredient. It will be understood, of course, that a choice of concentration of active ingredient depends upon the method of application as well as the type of composition and the degree of herbicidal control desired. In general, concentration is not critical within the range indicated since an effective quantity of active ingredient can be applied to a given area by applying greater quantities of a low concentration than of a higher concentration. The concentration of active ingredient in the dispersible powder and emulsifiable concentrates from which the aqueous compositions are prepared can be as high as 99.5% by weight. The concentration of active ingredient in the dust and granular formulations of the invention can vary from about 0.25 to about 80% or more, but advantageously is of the order of 0.50 to 20%.

The granular formulations of this invention are prepared with about 0.25 to about 80%, preferably 0.50 to 20% by weight, of active ingredient and a granular carrier, for example, vermiculite, pyrophyllite, or attapulgite. The active ingredient can be dissolved in a volatile solvent such as methylene chloride, acetone, and the like, and sprayed on the granular carrier as it is mixed and tumbled. The granules are then dried. The granular carrier can range in particle size from about 10 to about 60 mesh, preferably about 30 to 60 mesh.

The herbicidal dust compositions of the invention are prepared by intimate admixture of from about 0.25% to about 80% by weight, preferably 0.50 to 20% of the active ingredient with a solid pulverulent carrier which maintains the composition in a dry, free-flowing condition. The herbicidal dusts of the invention can be prepared by admixing the compound with a solid diluent and then milling. Preferably, however, the active ingredient is dissolved in a volatile organic solvent, of the kinds indicated above, and then sprayed on the solid carrier so as to assure thorough distribution. The mixture is then dried and milled to the desired size, e.g., less than about 60 microns.

Solid carriers that can be used in the dust compositions of the invention include the natural clays such as China clay and bentonite, minerals in the natural state such as talc, pyrophyllite, quartz, diatomaceous earth, fuller's earth, chalk, and rock phosphate, and the chemically modified minerals such as washed bentonite, precipitated calcium phosphate, precipitated calcium carbonate, precipitated calcium silicate, and colloidal silica. The solid diluents which can be employed in the compositions also include solid, compounded fertilizers. Such solid compositions can be applied to vegetation in the form of dusts by the use of conventional equipment.

A preferred composition, in accordance with the invention, is a dispersible powder which is prepared by incorporating a surfactant in a dust composition prepared as described above. Such a dispersible powder can be dispersed in water to any desired concentration and applied to vegetation by conventional spray equipment. Conveniently, the dispersible powders are formulated with higher concentrations of active ingredient than the dust compositions, for example, up to about 90%, preferably about 10 to 80%. Surfactants useful in preparing such dispersible powder compositions include alkyl sulfates and sulfonates, alkyl aryl sulfonates, sulfosuccinate esters, polyoxyethylene sulfates, polyoxyethylene-sorbitan monolaurate, alkyl aryl polyether sulfates, alkyl aryl polyether alcohols, alkyl naphthalene sulfonates, alkyl quaternary ammonium salts, sulfated fatty acids and esters, sulfated fatty acid amides, glycerol mannitan laurate, polyalkylether condensates of fatty acids, lignin sulfonates, and the like. A preferred class of surfactants includes blends of sulfonated oils and polyalcohol carboxylic acid esters (Emcol H-77), blends of polyoxyethylene ethers and oil-soluble sulfonates (Emcol H-400), blends of alkyl aryl sulfonates and alkylphenoxy polyethoxy ethanols (Tritons X-151, X-161, and X-171), e.g., about equal parts of sodium kerylbenzene sulfonate and isooctylphenoxy polyethoxy ethanol containing about 12 ethoxy groups, and blends of calcium alkyl aryl sulfonates and polyethoxylated vegetable oils (Agrimul $N_4S$). It will be understood, of course, that the sulfate and sulfonate surfactants suggested above will preferably be used in the form of their soluble salts, for example, their sodium salts. All of these surfactants are capable of reducing the surface tension of water to less than about 40 dynes per centimeter in concentrations of about 1% or less. The dispersible powder compositions can be formulated with a mixture of surfactants of the types indicated if desired.

A suitable dispersible powder formulation is obtained by blending and milling 235 lbs. of Georgia Clay, 5.5 lbs. of isooctylphenoxy polyethoxy ethanol (Triton X-100) as a wetting agent, 9.5 lbs. of a polymerized sodium salt of substituted benzoid long-chain sulfonic acid (Daxad 27) as a dispersing agent, and 250 lbs. of the active ingredient. The resulting formulation has the following percentage compositions (parts herein are by weight unless otherwise specified).

| | |
|---|---|
| Active ingredient | 50 % |
| Isooctylphenoxy polyethoxy ethanol | 1.1% |
| Polymerized sodium salt of substituted benzoic long-chain sulfonic acid | 1.9% |
| Georgia Clay | 47 % |

This formulation, when dispersed in water at the rate of 10 lbs. per 100 gals., gives a spray formulation containing about 0.6% (6000 ppm) active ingredient which can be applied to soil, plant growth media, growing plants, e.g., turf at the rate of 40 gals. per acre to give a total application of active ingredient of 2 lbs. per acre.

The compound of this invention can be applied to soil, plant growth media, growing plants, e.g., turf in aqueous sprays without a solid carrier. However, since the compound itself is relatively insoluble in water it is preferably dissolved in a suitable inert organic solvent carrier. Advantageously, the solvent carrier is immiscible with water so that an emulsion of the solvent carrier in water can be prepared. If, for example, a water-miscible solvent carrier such as acetone is used the solvent carrier will dissolve in the water and any excess according to Formula I will be thrown out of solution. In an emulsion, the solvent phase is dispersed in the water phase and the active ingredient is held in solution in the dispersed phase. In this way, uniform distribution of active ingredient with an aqueous spray can be achieved.

A solvent carrier in which the compound is highly soluble is desirable so that relatively high concentrations of active ingredient can be obtained. Sometimes, one or more solvent carriers with or without a cosolvent can be used in order to obtain concentrated solutions of the active ingredient, the main consideration being to employ a water-immiscible solvent for the active ingredient that will hold the compound in solution over the range of concentrations useful for preventing germination of undesired seeds and controlling growth of plants.

The emulsifiable concentrates of the invention are prepared by dissolving the active ingredient and a surfactant in a substantially water-immiscible solvent carrier (i.e., a solvent carrier which is soluble in water to the extent of less than 2.5% by volume at temperatures of the order of 20° to 30° C.), for example, cyclohexanone, methyl propyl ketone, summer oils, ethylene dichloride, aromatic hydrocarbons such as benzene, toluene, and xylene, and high-boiling petroleum hydrocarbons such as kerosene, diesel oil, and the like. If desired, a cosolvent such as methyl ethyl ketone, acetone, and the like can be included with the solvent carrier in order to enhance the solubility of the active ingredient. Aqueous emulsions are then prepared by mixing with water to give any desired concentration of active ingredient. The surfactants which can be employed in the aqueous emulsions of the invention are those types noted above. Mixtures of surfactants can be employed if desired.

Advantageously, the concentration of active ingredient in the emulsifiable concentrates can range from about 5% to about 50% by weight, preferably from about 10 to 40%. A concentrate comprising 20% (by weight) of the compound dissolved in a water-immiscible solvent of the kind noted above can be admixed with an aqueous medium in the proportions of 13 ml. of concentrate with 1 gal. of medium to give a mixture containing 700 parts of active ingredient per million parts of liquid carrier. Similarly, 1 qt. of a 20% concentrate mixed with 40 gals. of water provides about 1200 ppm of active ingredient. In the same manner, more concentrated solutions of active ingredient can be prepared.

The concentrate compositions of the invention which are intended for use in the form of aqueous dispersions or emulsions can also comprise a humectant, that is to say, an agent which will delay the drying of the composition in contact with material to which it has been applied. Suitable humectants include solubilized lignins, such as calcium lignosulfonate, and the like.

Further in accordance with this invention, certain formulations of 2-ethyl-4-methyl diester of 3,5-dimethyl-2,4-pyrroledicarboxylic acid with oil are particularly efficacious, and herbicidal action of the compound is improved. Any petroleum oil can be used so long as it is not so viscous as to be too difficult to disperse. A non-phytotoxic oil is satisfactory.

Advantageously, a 50% wettable powder of the herbicidal active ingredient is mixed with about 38 gals. water and 2 gals. oil for spray application. Alternatively, about 2 gals. oil and a 50% wettable powder are premixed and then dispersed in about 38 gals. water for spray application. In field tests, oil formulations of the foregoing type have given improved herbicidal action.

The rates of application to soils, plant growth media, growing plants, e.g., turf to be protected from noxious weeds will depend upon the species of vegetation to be controlled, the presence or absence of desirable species, the season of year at which treatment is undertaken, and the method and efficiency of application. In general, selective herbicidal activity is obtained when the compounds are applied at the rate of about 1.0 to about 15 lbs. per acre, preferably at the rate of about 1.0 to about 8 lbs. per acre.

The compositions containing 2-ethyl-4-methyl diester of 3,5-dimethyl-2,4-pyrroledicarboxylic acid can be applied to soil, plant growth media, growing plants, e.g., turf and bodies of water by conventional methods. For example, an area of soil can be treated prior to or after seeding by spraying wettable powder suspensions, emulsions, or solutions from boom-type power sprayers or from hand-operated knapsack sprayers. Dusts can be applied by power dusters, or by hand-operated dusters. Dusts and granular formulations can also be applied at the time of seeding in bands spanning the seeded rows.

The following examples are illustrative of the process and products of the present invention, but are not to be construed as limiting.

EXAMPLE 1

A dispersible powder concentrate having the following percentage composition:

| | |
|---|---|
| 2-ethyl 4-methyl diester of 3,5-dimethyl-2,4-pyrroledicarboxylic acid | 45.8% |
| Polymerized sodium salt of substituted benzoid long-chain sulfonic acid (Daxad 27) | 9.2% |
| Kaolinite | 45.0% | was prepared by mixing 250 g. of 2-ethyl-4-methyl diester of 3,5-dimethyl-2,4-pyrroledicarboxylic acid, 50 g. of a polymerized sodium salt of substituted benzoid long-chain sulfonic acid (Daxad 27), and 245 g. of kaolinite. The mixture was milled to a particle size averaging 5 to 30 microns. It was suspended in 10 gals. of water, giving an aqueous spray containing about 6500 parts per million of active ingredient.

EXAMPLE 2

A fine granular formulation having the following percentage composition:

| | |
|---|---|
| 2-ethyl-4-methyl diester of 3,5-dimethyl-2,4-pyrroledicarboxylic acid | 3.7% |
| Vermiculite (30/60 mesh) | 96.3% | was prepared by spraying a solution of 220 g. of 2-ethyl-4-methyl diester of 3,5-dimethyl-2,4-pyrroledicarboxylic acid in 1000 ml. of methylene chloride onto 5780 g. of vermiculite (30 to 60 mesh) while the vermiculite was being tumbled and stirred so as to assure even distribution. The methylene chloride was then evaporated, leaving the active compound adsorbed on the vermiculite, and the vermiculite was pulverized.

EXAMPLE 3

An emulsifiable concentrate having the following percentage composition:

| | |
|---|---|
| 2-ethyl-4-methyl diester of 3,5-dimethyl-2,4-pyrrolecarboxylic acid | 15.0% |
| Technical alkyl naphthalene boiling at 238° to 293° C. (Velsicol AR50) | 19.7% |
| Xylene | 17.4% |
| Acetone | 17.4% |
| Ethylene dichloride | 25.4% |
| Blend of alkyl aryl sulfonates and alkylphenoxy polyethoxy ethanols (Triton X-151) | 5.1% | was prepared by mixing 15.0 lbs. of 2-ethyl-4-methyl diester of 3,5-dimethyl-2,4-pyrroledicarboxylic acid, 19.7 lbs. of Velsicol AR50, 17.4 lbs. of xylene, 17.4 lbs. of acetone, 25.4 lbs. of ethylene dichloride, and 5.1 lbs. of Triton X-151.

6.67 lbs. of the concentrate mixed with 10 gals. of water gave a spray emulsion containing about 11,000 ppm of active ingredient.

EXAMPLE 4

An emulsifiable concentrate having the following percentage composition:

| | |
|---|---|
| 2-ethyl-4-methyl diester of 3,5-dimethyl-2,4-pyrroledicarboxylic acid | 40.0% |
| Technical alkyl naphthalene boiling at 238° to 293° C. (Velsicol Ar50) | 13.7% |
| Xylene | 12.3% |
| Acetone | 11.3% |
| Ethylene dichloride | 17.7% |
| Blend of alkyl aryl sulfonates and alkylphenoxy polyethoxy ethanols (Triton X-151) | 5.0% | was prepared by mixing 40.0 lbs. of 2-ethyl-4-methyl diester of 3,5-dimethyl-2,4-pyrroledicarboxylic acid, 13.7 lbs. of Velsicol AR50, 12.3 lbs. of xylene, 11.3 lbs. of acetone, 17.7 lbs. of ethylene dichloride, and 5.0 lbs. of Triton X-151.

1.67 lbs. of the concentrate mixed with 10 gals. of water gave a spray emulsion containing about 8,000 ppm of active ingredient.

EXAMPLE 5

A dispersible powder concentrate having the following percentage composition:

| | |
|---|---|
| 2-ethyl-4-methyl diester of 3,5-dimethyl-2,4-pyrrole-dicarboxylic acid | 50% |
| Kaolinite clay (finely divided) | 46% |
| Sodium salt of condensed mono-naphthalene sulfonic acid (Lomar D) | 4% | was prepared by mixing 50 g. of 2-ethyl-4-methyl diester of 3,5-dimethyl-2,4-pyrroledicarboxylic acid, 46 g. of the kaolinite clay, and 4 g. of Lomar D. The mixture was milled to an average particle size of 5 to 30 microns.

EXAMPLE 6

A granular formulation having the following percentage composition:

| | |
|---|---|
| 2-ethyl-4-methyl diester of 3,5-dimethyl-2,4-pyrrole-dicarboxylic acid | 1% |
| Pyrophyllite (30/60 mesh) | 99% | was prepared by dissolving 1.0 lb. of 2-ethyl-4-methyl diester of 3,5-dimethyl-2,4-pyrroledicarboxylic acid in 10.0 l. of ethylene dichloride and spraying the solution on 99.0 lbs. of pyrophyllite. The granules were dried and then packaged for use.

EXAMPLE 7

In a test, various amounts of 2-ethyl-4-methyl diester of 3,5-dimethyl-2,4-pyrroledicarboxylic acid were applied to substantially uniform volumes of a pond compartmented by plastic partitions. Each compartment had 20 sq. ft. of surface area and water depth was 3 ft. Each had about the same association of aquatic plant life, particularly plankton and filamentous algae. The compound was applied by underwater injection in amounts calculated to obtain concentrations of 2 ppm, 1 ppm, 0.5 ppm, and 0.25 ppm.

After 6 weeks, during midsummer, the control of plankton and filamentous algae was observed to be 100, 90, 30%, and imperceptible, respectively.

I claim:

1. A herbicidal composition comprising a dispersible carrier and a herbicidally effective amount of 2-ethyl-4-methyl diester of 3,5-dimethyl-2,4-pyrroledicarboxylic acid wherein the "dispersible carrier" is a solid pulverulent carrier with an average particle size less than 60 microns.

2. Composition according to claim 1 comprising a surfactant.

3. A herbicidal composition comprising a dispersible carrier and a herbicidally effective amount of 2-ethyl-4-methyl diester of 3,5-dimethyl-2,4-pyrroledicarboxylic acid wherein the "dispersible carrier" comprises a substantially water-immiscible solvent carrier and a surfactant.

4. A composition according to claim 2 wherein the "dispersible carrier" is a granular carrier of from about 10 to about 60 mesh.

5. Herbicidal composition comprising a herbicidally effective amount of 2-ethyl-4-methyl diester of 3,5-dimethyl-2,4-pyrroledicarboxylic acid as the active ingredient, a substantial amount of a solid pulverulent carrier having an average particle size less than 60 microns, a surfactant, and a substantial amount of a petroleum oil.

* * * * *